US006369029B1

(12) United States Patent
Andress et al.

(10) Patent No.: US 6,369,029 B1
(45) Date of Patent: Apr. 9, 2002

(54) METHOD OF STIMULATING OSTEOGENESIS USING A C-TERMINALLY TRUNCATED INSULIN-LIKE GROWTH FACTOR BINDING PROTEIN-5 (IGFBP-5)

(75) Inventors: Dennis L. Andress, 1651 22nd Ave. East, Seattle, WA (US) 98112; Michael C. Kiefer, Clayton, CA (US)

(73) Assignees: Chiron Corporation, Emeryville, CA (US); Dennis L. Andress, Seattle, WA (US)

( * ) Notice: Subject to any disclaimer, the term of this patent is extended or adjusted under 35 U.S.C. 154(b) by 0 days.

(21) Appl. No.: 08/456,640

(22) Filed: Jun. 2, 1995

Related U.S. Application Data

(62) Division of application No. 07/972,142, filed on Nov. 4, 1992, now abandoned.

(51) Int. Cl.[7] .................. A61K 38/18; A61K 38/23; A61K 38/30; C07K 14/475
(52) U.S. Cl. ................. 514/12; 514/2; 530/399
(58) Field of Search ................ 514/2, 12; 530/350, 530/399

(56) References Cited

U.S. PATENT DOCUMENTS 5,118,667 A * 6/1992 Adams et al. ................ 514/12

FOREIGN PATENT DOCUMENTS

| WO | WO 89/08667 | 9/1989 |
| WO | WO 89/09268 | 10/1989 |
| WO | WO 89/09792 | 10/1989 |
| WO | WO 90/00569 | 1/1990 |
| WO | WO 92/03152 | 3/1992 |
| WO | WO 92/03469 | 3/1992 |
| WO | WO 92/03470 | 3/1992 |
| WO | WO 92/03471 | 3/1992 |
| WO | WO 92/12243 | 7/1992 |
| WO | WO 92/14834 | 9/1992 |

OTHER PUBLICATIONS

Bennett et al. Am. J. Surg. 165: 728–737, 1993.*
Robson et al. Introduction to Proteins and Protein Engineering. Elsevier, NY, p. 41, 1986.*
Ngo et al. Computational Complexity, Protein Structure Prediction, and the Levinthal Paradox. The Protein Folding Problem and Teriary Structure Prediction. Birkhauser Boston, pp. 491–495, 1994.*
Bowie et al. Deciphering the Message in Protein Sequences: Tolerance to Amino Acid Substitutions, Science, vol. 247: 1306–1310, 1990.*
Wells. Additivity of Mutational Effects in Proteins. Biochemistry, 29(37): 8509–8517, 1990.*
Michael C. Kiefer et al., "Characterization of Recombinant Human Insulin–like Growth Factor Binding Proteins 4, 5, and 6 Produced in Yeast," *The Jrnl. of Biological Chem.* (1992) 267(18):12692–12699.

Kiefer et al., "Molecular Cloning of a New Human Insulin-Like Growth Factor Binding Protein," *Biochem. and Biophys. Res. Commun.* 176(1):219–226 (1991).
Andress et al., *Biochem. and Biophys. Res. Comm.* 176:213–218 (1991).
Andress et al., "Human Osteoblast–Derived Insulin–Like Growth Factor (IGF) Binding Protein–5 Stimulates Osteoblast Mitogenesis and Potentiates IGF Action," *J. Biol. Chem.* 267(31):22467–22472 (1992).
Andress et al., "Carboxy–Truncated Insulin–Like Growth Factor Binding Protein–5 Stimulates Mitogenesis in Osteoblast–Like Cells," *Biochem. and Biophys. Res. Comm.* 195(1):25–30 (1993).
Bar et al., *Endocrinology* 125(4):1910–1920 (1989).
Baustista et al., *Biochem. Biophys. Res. Commun.* 176(7):756–763 (1990).
Baxter et al., *Bioch. Biophys. Res. Com.* 139:1256–1261 (1986).
Binkert et al., *The EMBO Journal* 8:2497–2502 (1989).
Brinkman et al., "Mutations in the C–Terminal Part of Insulin–Like Growth Factor (IGF)–Binding Protein–1 Result in Dimer Formation and Loss of IGF Binding Capacity," *Mol. Endocrinol.* 5(7):987–994 (1991).
Clemmons et al., *Modern Concepts of Insulin–Like Growth Factors* pp. 475–486 (1991).
Ebeling et al., "Short–Term Effects of Recombinant Human Insulin–Like Growth Factor–Ion Bone Turnover in Normal Women," *J. Bone Min. Res.* 7:S138, Abstract 184 (1992).
Guler et al., "Recombinant Human Insulin–Like Growth Factor I Stimulates Growth and has Distinct Effects on Organ Size in Hypophysectomized Rats," *Proc. Natl. Acad. Sci. USA* 85:4889–4893 (1988).
Hock et al., "Insulin–Like Growth Factor I Has Independent Effects on Bone Matrix Formation and Cell Replication," *Chemical Abstracts* 108:154 (1988).
Johansson et al., "Insulin–Like Growth Factor I Stimulates Bone Turnover is Osteoporosis," *Lancet* 339:1619 (1992).
LaTour et al., *Mol. Endocrinol.* 4:1806–1814 (1990).
Merimee et al., "Insulin–Like Growth Factors in Pygmies, The Role of Puberty in Determining Final Stature," *New Eng. J. Med.* 15:906–911 (1987).
Mohan et al., *Proc. Natl. Acad. Sci.* 86:8338–8342 (1989).
Mohan et al., "Studies on the Mechanisms by Which Insulin–Like Growth Factor (IGF) Binding Protein–4 (IGFBP–4) and IGFBP–5 Modulate IGF Actions in Bone Cells," *Journal of Biological Chemistry* 270(35):20424–20431 (1995).

(List continued on next page.)

*Primary Examiner*—Christine J. Saoud
(74) *Attorney, Agent, or Firm*—Roberta L. Robins; Joseph H. Guth; Robert P. Blackburn

(57) ABSTRACT

Methods for stimulating osteogenesis using C-terminally truncated insulin-like growth factor binding protein-5 (IGFBP-5) compounds and derivatives thereof are described. The IGFBP-5 polypeptides used in the methods are mitogenic and can be combined in compositions with insulin-like growth factor (IGF).

15 Claims, 3 Drawing Sheets

OTHER PUBLICATIONS

Mueller et al., "Insulin–Like Growth Factor–1 Increases Trabecular Bone Mass in the Ovariectomized Rat," *J. Bone Mineral Res.* Suppl. A, F–221, Abstract 549 (1991).

Schmid et al., *Bioch. Biophys. Res. Com.* 179:579–585 (1991).

Shimasaki et al., *Mol. Endocrinol.* 4:1451–1458 (1990).

Shimasaki et al., 2nd International IGF Symposium Abstract (Jan. 1991), discussed amno terminal mino acids for IGFBP–4, IGFBP–5, and IGFBP–6.

Shimasaki et al., *J. Biol. Chem.* 266:10646–10653 (1991).

Shimasaki et al., *Mol. Endocrinol.* 5:938–948 (1991).

Shimonka et al., *Biochem. Biophys. Res. Commun.* 165(1):189–195 (1989).

Simpson, "Growth Factors Which Affect Bone," *Physiol.* 235:527–530 (1984).

Wood et al., *Mol. Endocrinol.* 2:1176–1185 (1988).

Zapf et al., *Biochem. Biophys. Res. Commun.* 156(3):1187–1194 (1988).

Zapf et al., *J. of Biol. Chem.* 265;14892–14898 (1990).

* cited by examiner

Argument Map in DNA Strand pBsBP6-1A = from the '/arp/lib/6mers' file.
Translation shown at frame 3.

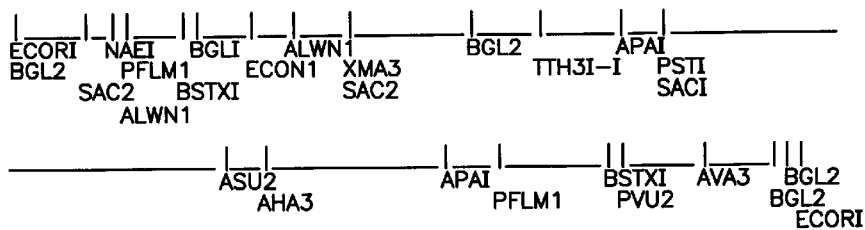

```
          cloning linker
 3GAATTCGGAGATCTACAGGCTCTCCTGCCCCACCCCGAGGTAAAGGGGGCGACTAAGAGAAG
  TAAGCCTCTAGATGTCCGAGAGGACGGGGTGGGGCTCCATTTCCCCCGCTGATTCTCTTC
   ^    ^              ^

1 ECORI, 9 BGL2,

MetValLeuLeuThrAlaValLeuLeuLeuLeuAlaAlaTyrAlaGlyProAlaGlnSer
 63 ATGGTGTTGCTCACCGCGGTCCTCCTGCTGCTGGCCGCCTATGCGGGGCCGGCCCAGAGC
    TACCACAACGAGTGGCGCCAGGAGGACGACGACCGGCGGATACGCCCCGGCCGGGTCTCG
                                               ^        ^  ^^

76 SAC2, 110 NAEI, 116 PFLM1, 117 ALWN1,

LeuGlySerPheValHisCysGluProCysAspGluLysAlaLeuSerMetCysProPro
123 CTGGGCTCCTTCGTGCACTGCGAGCCCTGCGACGAGAAAGCCCTCTCCATGTGCCCCCCC
    GACCCGAGGAAGCACGTGACGCTCGGGACGCTGCTCTTTCGGGAGAGGTACACGGGGGGG
                                                               ^

181 BSTXI,

SerProLeuGlyCysGluLeuValLysGluProGlyCysGlyCysCysMetThrCysAla
183 AGCCCCCTGGGCTGCGAGCTGGTCAAGGAGCCGGGCTGCGGCTGCTGCATGACCTGCGCC
    TCGGGGGACCCGACGCTCGACCAGTTCCTCGGCCCGACGCCGACGACGTACTGGACGCGG
    ^                                                          ^

184 BGLI, 242 ECON1,

LeuAlaGluGlyGlnSerCysGlyValTyrThrGluArgCysAlaGlnGlyLeuArgCys
243 CTGGCCGAGGGGCAGTCGTGCGGCGTCTACACCGAGCGCTGCGCCCAGGGGCTGCGCTGC
    GACCGGCTCCCCGTCAGCACGCCGCAGATGTGGCTCGCGACGCGGGTCCCCGACGCGACG
                                                   ^

288 ALWN1,

LeuProArgGlnAspGluGluLysProLeuHisAlaLeuLeuHisGlyArgGlyValCys
303 CTCCCCCGGCAGGACGAGGAGAAGCCGCTGCACGCCCTGCTGCACGGCCGCGGGGTTTGC
    GAGGGGGCCGTCCTGCTCCTCTTCGGCGACGTGCGGGACGACGTGCCGGCGCCCCAAACG
                                                    ^   ^

347 XMA3, 350 SAC2,

LeuAsnGluLysSerTyrArgGluGlnValLysIleGluArgAspSerArgGluHisGlu
363 CTCAACGAAAAGAGCTACCGCGAGCAAGTCAAGATCGAGAGAGACTCCCGTGAGCACGAG
    GAGTTGCTTTTCTCGATGGCGCTCGTTCAGTTCTAGCTCTCTCTGAGGGCACTCGTGCTC

GluProThrThrSerGluMetAlaGluGluThrTyrSerProLysIlePheArgProLys
423 GAGCCCACCACCTCTGAGATGGCCGAGGAGACCTACTCCCCCAAGATCTTCCGGCCCAAA
    CTCGGGTGGTGGAGACTCTACCGGCTCCTCTGGATGAGGGGGTTCTAGAAGGCCGGGTTT
                                                   ^

466 BGL2,
```

FIG. 1A

```
        HisThrArgIleSerGluLeuLysAlaGluAlaValLysLysAspArgArgLysLysLeu
483 CACACCCGCATCTCCGAGCTGAAGGCTGAAGCAGTGAAGAAGGACCGCAGAAAGAAGCTG
    GTGTGGGCGTAGAGGCTCGACTTCCGACTTCGTCACTTCTTCCTGGCGTCTTTCTTCGAC
                                                              ^
    542 TTH3I,
        ↓
        ThrGlnSerLysPheValGlyGlyAlaGluAsnThrAlaHisProArgIleIleSerAla
543 ACCCAGTCCAAGTTTGTCGGGGGAGCCGAGAACACTGCCCACCCCCGGATCATCTCTGCA
    TGGGTCAGGTTCAAACAGCCCCCTCGGCTCTTGTGACGGGTGGGGGCCTAGTAGAGACGT

ProGluMetArgGlnGluSerGluGlnGlyProCysArgArgHisMetGluAlaSerLeu
603 CCTGAGATGAGACAGGAGTCTGAGCAGGGCCCCTGCCGCAGACACATGGAGGCTTCCCTG
    GGACTCTACTCTGTCCTCAGACTCGTCCCGGGGACGGCGTCTGTGTACCTCCGAAGGGAC
                                  ^                         ^
    629 APAI,  660 PSTI,

GlnGluLeuLysAlaSerProArgMetValProArgAlaValTyrLeuProAsnCysAsp
663 CAGGAGCTCAAAGCCAGCCCACGCATGGTGCCCCGTGCTGTGTACCTGCCCAATTGTGAC
    GTCCTCGAGTTTCGGTCGGGTGCGTACCACGGGGCACGACACATGGACGGGTTAACACTG
       ^
    666 SACI,

ArgLysGlyPheTyrLysArgLysGlnCysLysProSerArgGlyArgLysArgGlyIle
723 CGCAAAGGATTCTACAAGAGAAAGCAGTGCAAACCTTCCCGTGGCCGCAAGCGTGGCATC
    GCGTTTCCTAAGATGTTCTCTTTCGTCACGTTTGGAAGGGCACCGGCGTTCGCACCGTAG

CysTrpCysValAspLysTyrGlyMetLysLeuProGlyMetGluTyrValAspGlyAsp
783 TGCTGGTGCGTGGACAAGTACGGGATGAAGCTGCCAGGCATGGAGTACGTTGACGGGGAC
    ACGACCACGCACCTGTTCATGCCCTACTTCGACGGTCCGTACCTCATGCAACTGCCCCTG

PheGlnCysHisThrPheAspSerSerAsnValGluOP
843 TTTCAGTGCCACACCTTCGACAGCAGCAACGTTGAGTGATGCGTCCCCCCCCAACCTTTC
    AAAGTCACGGTGTGGAAGCTGTCGTCGTTGCAACTCACTACGCAGGGGGGGGTTGGAAAG

903 CCTCACCCCCTCCCACCCCCAGCCCCGACTCCAGCCAGCGCCTCCCTCCACCCCAGGACG
    GGAGTGGGGGAGGGTGGGGGTCGGGGCTGAGGTCGGTCGCGGAGGGAGGTGGGGTCCTGC

963 CCACTCATTTCATCTCATTTAAGGGAAAAATATATATCTATCTATTTGAGGAAACTGAGG
    GGTGAGTAAAGTAGAGTAAATTCCCTTTTTATATATAGATAGATAAACTCCTTTGACTCC

1023 ACCTCGGAATCTCTAGCAAGGGCTCAACTTCGAAAATGGCAACAACAGAGATGCAAAAAG
     TGGAGCCTTAGAGATCGTTCCCGAGTTGAAGCTTTTACCGTTGTTGTCTCTACGTTTTTC
                                        ^
     1051 ASU2,

1083 CTAAAAGACACCCCCCCCTTTAAATGGTTTTCTTTTTGAGGCAAGTTGGATGAACAGA
     GATTTTTCTGTGGGGGGGGAAATTTACCAAAAGAAAAACTCCGTTCAACCTACTTGTCT
                      ^
     1103 AHA3,

1143 GAAGGGAAGAGAGGAAGAACGAGAGGAAGAGAAGGGAAGGAAGTGTTTGTGTAGAAGAGA
     CTTCCCTTCTCTCCTTCTTGCTCTCCTTCTCTTCCCTTCCTTCACAAACACATCTTCTCT

1203 GAGAAAGACGAATAGAGTTAGGAAAAGGAAGACAAGCAGGTGGGCAGGAAGGACATGCAC
     CTCTTTCTGCTTATCTCAATCCTTTTCCTTCTGTTCGTCCACCCGTCCTTCCTGTACGTG
```

FIG. 1B

1263 CGAGACCAGGCAGGGGCCCAACTTTCACGTCCAGCCCTGGCCTGGGGTCGGGAGAGGTGG
     GCTCTGGTCCGTCCCCGGGTTGAAAGTGCAGGTCGGGACCGGACCCCAGCCCTCTCCACC

1276 APAI,

1323 GCGCTAGAAGATGCAGCCCAGGATGTGGCAATCAATGACACTATTGGGGTTTCCCAGGAT
     CGCGATCTTCTACGTCGGGTCCTACACCGTTAGTTACTGTGATAACCCCAAAGGGTCCTA

1340 PFLM1,

1383 GGATTGGTCAGGGGGAGAAAGGAAAAGGCAAAACACTCCAGGACCTCTCCCGGATCTGTC
     CCTAACCAGTCCCCCTCTTTCCTTTTCCGTTTTGTGAGGTCCTGGAGAGGGCCTAGACAG

1443 TCCTCCTCTAGCCAGCAGTATGGACAGCTGGACCCCTGAACTTCCTCTCCTCTTACCTGG
     AGGAGGAGATCGGTCGTCATACCTGTCGACCTGGGGACTTGAAGGAGAGGAGAATGGACC

1454 BSTXI, 1467 PVU2,

1503 GCAGAGTGTTGTCTCTCCCCAAATTTATAAAAACTAAAATGCATTCCATTCCTCTGAAAG
     CGTCTCACAACAGAGAGGGGTTTAAATATTTTTGATTTTACGTAAGGTAAGGAGACTTTC

1541 AVA3,

1563 CAAAACAAATTCATAATTGAGTGATATTAAATAGAGAGGTTTTCGGAAGCAGATCTGTGA
     GTTTTGTTTAAGTATTAACTCACTATAATTTATCTCTCCAAAAGCCTTCGTCTAGACACT

1613 BGL2,

1623 ATATGAAATCCTGTAGATCTCCGAATTC
     TATACTTTAGGACATCTAGAGGCTTAAG

1637 BGL2, 1645 ECORI,

FIG. 1C

METHOD OF STIMULATING OSTEOGENESIS USING A C-TERMINALLY TRUNCATED INSULIN-LIKE GROWTH FACTOR BINDING PROTEIN-5 (IGFBP-5)

This is a divisional of U.S. application Ser. No. 07/972,142, filed Nov. 4, 1992, now abandoned.

BACKGROUND OF THE INVENTION

1. Field of the Disclosure

The present invention relates generally to insulin-like growth factor binding proteins (IGFBPs) and, more specifically, to truncated IGFBPs having decreased affinity for IGFs and mitogenic activity.

2. Description of the Related Art

Insulin-like growth factors (IGFs) are low molecular weight polypeptide hormones with structural homology to proinsulin. Two different IGFs are known, namely IGF-I and IGF-II, which are mitogenic in vitro for a wide variety of cells in tissue culture. Both IGFs stimulate in vitro the growth of various tissues and in particular they induce collagen synthesis. IGF-I mediates the growth promoting effect of growth hormone in chondrogenesis and bone formation and is therefore essential for normal growth of an individual. This is demonstrated by the fact that pygmies and toy poodles are deficient in IGF-I but have normal growth hormone level in their serum. IGF-II is believed to play a key role in fetal development and nerve growth.

IGFs stimulate cell growth in a variety of tissues including bone. The growth stimulatory effects of IGF-I and IGF-II in bone have been shown for cells of the osteoblast lineage. Because both IGFs are secreted by this cell type and both are recoverable from bone matrix, they are capable of affecting osteoblast function through autocrine or paracrine mechanisms. Factors that regulate IGF effects in osteoblasts are not completely understood. Regulation of IGF receptor affinity is a well documented mechanism that potentially modulates autocrine-directed cell growth.

Through their association with carrier proteins (hereinafter referred to as IGF binding proteins or IGFBPs), binding of IGFs to cell surface receptors is inhibited. It has also been demonstrated that another function of the IGFBPs is to increase the short half-life of IGFs, which are subjected to rapid proteolytic degradation when present in the free form in blood. IGFs for use in the above-referred treatments are advantageously administered to a subject in association with at least one IGF binding protein.

IGFBPs are secreted by cells in culture and either inhibit or enhance IGF-stimulated functions [Clemmons, D. R., et al., (1991) In Modern Concepts of Insulin-like Growth Factors. E. M. Spencer, editor. Elsevier, New York, N.Y. 475–486]. Known forms of IGFBPs include IGFBP-1, having a molecular weight of approximately 30–40 kd in humans. See, e.g., WO89/09792, published Oct. 19, 1990, Clemmons, D. R., et al., pertaining to CDNA sequences and cloning vectors for IGFBP-1 and IGFBP-2; WO89/08667, published Sep. 21, 1989, Drop, L. S., et al., relating to an amino acid sequence of IGFBP-1; WO89/09268, published Oct. 5, 1989, Baxter, R. C., relating to a CDNA sequence of IGFBP-1 and methods of expression for IGFBP-1.

IGFBP-2 has a molecular weight of approximately 33–36 kd. See, e.g., Binkert, C. et al., The EMBO Journal (1989) 8:2497–2502, relating to a nucleotide and deduced amino acid sequence for IGFBP-2.

IGFBP-3 has a molecular weight of 150 kd. See, e.g., Baxter, R. C. et al., Bioch. Biophys. Res. Com. (1986) 139:1256–1261, pertaining to a 53 kd subunit of IGFBP-3 that was purified from human serum; Wood, W. I. et al., Mol. Endocrinol. (1988) 2:1176–1185, relating to a full length amino acid sequence for IGFBP-3 and cellular expression of the cloned IGFBP-3 cDNA in mammalian tissue culture cells; WO90/00569, published Jan. 25, 1990, Baxter, R. C., relating to isolating from human plasma an acid-labile subunit (ALS) of IGFBP complex and the particular amino acid sequence for ALS pertaining to a subunit of IGFBP-3; Schmid, Ch. et al., Bioch. Biophys. Res Com. (1991) 179:579–585, relates to effects of full length and truncated IGFBP-3 effect on two different osteoblastic cell lines.

Although initially some inconsistencies in nomenclature for IGFBP-4, IGFBP-5, and IGFBP-6 existed, in 1991 participants of the 2 nd International IGF Symposium agreed upon an accepted IGFBP-4, IGFBP-5, and IGFBP-6 nomenclature. Using accepted terminology, Mohan, S. et al., Proc. Natl. Acad. Sci. (1989) 86:8338–8342, relates to an N-terminal amino acid sequence for an IGFBP-4 isolated from medium conditioned by human osteosarcoma cells, and Shimasaki, S. et al., Mol. Endocrinology (1990) 4:1451–1458, pertains to IGFBP cDNAs encoding IGFBP-4 from rat and human. WO92/03471 published Mar. 5, 1992, Kiefer et al., relates to a new insulin-like growth factor binding protein IGFBP-4 (originally designated therein as IGFBP-5); and WO92/03470 published Mar. 5, 1992, Kiefer et al., relates to genetic material encoding IGFBP-4 (originally designated therein as IGFBP-5).

WO92/12243 published Jul. 23, 1992, Kiefer et al., relates to a new insulin-like growth factor binding protein IGFBP-5 (originally designated therein as IGFBP-6). Andress, D. L. et al., Bioch. Biophys. Res Com. (1991) 176:213–218 relates to the modulation of cellular action of a mixture of affinity-purified IGFBPs from a U-2 cell conditioned media on IGFs.

WO92/03469 published Mar. 5, 1992, Kiefer et al., relates to genetic material encoding IGFBP-6 (originally designated therein as IGFBP-4); and WO92/03152 published Mar. 5, 1992, Kiefer et al., relates to a new insulin-like growth factor IGFBP-6. (originally designated therein as IGFBP-4).

Zapf, J. et al., J. of Biol. Chem. (1990) 265:14892–14898, pertains to four IGFBPs (IGFBP-2, IGFBP-3, a truncated form of IGFBP-3, and IGFBP-4) isolated from adult human serum by insulin-like growth factor (IGF) affinity chromatography and high performance liquid chromatography. Shimasaki, et al., 2nd International IGF Symposium Abstract (January 1991), discussed amino terminal amino acids for IGFBP-4, IGFBP-5, and IGFBP-6.

When administered alone, i.e., without any IGF, the IGFBPs may also be therapeutically useful for blocking the adverse effects of IGFs, such as those which occur when IGFs are produced in excess, e.g. free IGFs secreted by certain cancer cells such as hormone-producing cancer cells such as breast or kidney cancer cells. More recently, it was demonstrated that U-2 human osteosarcoma cells secrete IGFBP-5 and IGFBP-6 [Andress, D. L., and Birnbaum, R. S. (1991) Biochem. Biophys. Res. Commun. 176, 213–218; Shimasaki, S., et al. (1991) J. Biol. Chem. 266, 10646–10653; Shimasaki, S., et al. (1991) Mol. Endocrinol. 5, 938–948]. Although affinity-purified IGF-binding proteins derived from U-2 conditioned medium clearly enhanced IGF-I stimulated mitogenesis [Andress, D. L., and Birnbaum, R. S. (1991) Biochem. Biophys. Res. Commun. 176, 213–218], it was unclear from those studies which protein was responsible for this effect. Mohan et al. demonstrated that IGFBP-4, purified from TE-89 human osteosarcoma cells inhibits IGF-stimulated osteoblast mitogenesis. [Mohan, S., et al. (1989) Proc. Natl. Acad. Sci. (U.S.A.). 86, 8338–8342; see also LaTour, D., et al. (1990) Mol. Endocrinol. 4, 1806–1814].

There is significant interest in the discovery of new properties and applications for known IGFBPs in the presence or absence of IGF.

SUMMARY OF THE INVENTION

It has been surprisingly discovered that truncated IGFBPs possess mitogenic and osteogenic activity. This discovery has led to the present invention of promoting, for example, bone growth both in vitro and in vivo. Generally, these truncated IGFBPs exhibit reduced affinity for IGFs. Accordingly, it is an object of the present invention to provide a truncated IGFBP that has a decreased affinity for insulin-like growth factors (IGFs) and/or is capable of stimulating mitogenesis in the presence or absence of exogenous or endogenous IGFs.

The present invention provides truncated IGFBPs using recombinant. DNA molecules capable of expressing the truncated IGFBP and also compounds comprising a truncated IGFBP capable of promoting growth of bone cells, preferably with a pharmaceutically acceptable carrier.

The present invention also provides DNA molecules encoding a truncated IGFBP, which may be used to construct vectors for expression in host systems by recombinant DNA techniques.

Additionally, methods for treating bone disorders and stimulating mitogenic activity in mammals, preferably humans, are provided.

BRIEF DESCRIPTION OF THE DRAWING

FIGS. 1A–1C are a schematic diagram showing the nucleotide sequences of a clone encoding human IGFBP-5 and a truncated form as well as the encoded amino acid sequence nucleotides 1–19 of the sequence represent the cloning linker. A map showing the restriction sites is depicted above the sequence.

DESCRIPTION OF SPECIFIC EMBODIMENTS

The present invention relates generally to truncated IGFBPs having decreased affinity for IGFs and intrinsic activity in stimulating cell growth in a variety of tissues.

1. Definitions

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

Standard abbreviations for nucleotides and amino acids are used in FIG. 1 and elsewhere in this specification. All publications, patents, and patent applications cited herein are incorporated by reference.

"IGF" refers to IGF-I and IGF-II. IGF-I is described in Rinderknecht, E. and Humbel, R. E., J. Biol. Chem. (1978) 253:2769. IGF-II is described in Rinderknecht, E. and Humbel, R. E., FEBS (1978) 89:283. "IGF" also includes any derivative or fragment of IGF-I or IGF-II having an insulin-like growth factor activity.

As used herein, the term "insulin-like growth factor binding protein" or "IGFBP" relates to a group of structurally distinct proteins displaying degrees of sequence homology suggesting they are encoded by a related family of genes and that they are capable of binding an antibody specific for that particular IGFBP or to an IGF. See, e.g., the publications and patents cited above.

Examples of IGFBPs that can be used in truncated compounds of the present invention include polypeptides with minor amino acid variations from the natural amino acid sequence of IGFBPs; in particular, conservative amino acid replacements are contemplated. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an aspartate with a glutamate, a threonine with a serine, or a similar conservative replacement of an amino acid with a structurally related amino acid will not have a major effect on the biological activity. Polypeptide molecules having substantially the same amino acid sequence as IGFBPs but possessing minor amino acid substitutions that do not substantially affect either (i) the IGFBP's mitogenic activity, and/or (ii) the ability of the IGFBP polypeptide derivatives-to interact with IGFBP-specific molecules, such as antibodies and IGF molecules, particularly IGF-I and especially IGF-II, are within the definition of IGFBPs. Derivatives include aggregative conjugates with other IGFBP molecules and covalent conjugates with unrelated chemical moieties. Covalent derivatives are prepared by linkage of functionalities to groups which are found in IGFBP amino acid chains or at the N- or C-terminal residues by means known in the art.

A significant advantage of producing IGFBPs by recombinant DNA techniques rather than by isolating and purifying a IGFBP from natural sources is that equivalent quantities of IGFBP can be produced by using less starting material than would be required for isolating the IGFBP from a natural source. Producing IGFBP by recombinant techniques also permits the IGFBP to be isolated in the absence of some molecules normally present in cells. Indeed, IGFBP compositions entirely free of any trace of human protein contaminants can readily be produced because the only human protein produced by the recombinant non-human host is the recombinant IGFBP. Potential viral agents from natural sources and viral components pathogenic to humans are also avoided. It is also apparent that recombinant DNA techniques can be used to produce IGFBP polypeptide derivatives that are not found in nature, such as the variations described above. IGFBP-specific molecules include polypeptides such as antibodies that are specific for the IGFBP polypeptide containing the naturally occurring truncated IGFBP amino acid sequence.

A "truncated" IGFBP includes the genus of truncations wherein a) there is decreased binding affinity for IGF and/or b) the truncated IGFBP demonstrates mitogenic activity, especially osteogenic activity and/or bone formation. Routine screening methods to determine the above-cited properties are known by one of ordinary skill in the art, see Modrowski, et al., J. Bone & Min. Res. 7:961–969, which relates to assays which measure increased bone formation and increased osteoblasts in bone. Preferred truncations include, but is not limited to, truncations at the C-terminus, (or "carboxyl end") NH2-terminus, or truncations within the IGFBP molecule and variations thereof. Generally, at least about 25 amino acids, preferably about 50 amino acids, and most preferably at least about 75 amino acids are deleted by the truncation. Even larger truncations (e.g., about 100 or more, about 125 or more, or even about 150 or more amino acids) can be employed.

A preferred truncation is an IGFBP selected from a group consisting of an IGFBP having an amino acid sequence truncated at the C-terminus which is truncated at least between amino acid 100 and 300 and more preferably between amino acid 150 and amino acid 250 and most preferably at about amino acid 160 of the IGFBP amino acid sequence.

When designing truncated proteins, several of the IGFBPs are preferred, such as IGFBP-1-2, and IGFBP-4-6. Particularly prefered in the practice of this invention is IGFBP-5. A cDNA encoding a preferred truncated IGFBP-5 is presented in FIG. 1. Other species of truncated IGFBP-5 exist or can be created by routine methods. In the sequence shown, the cleavage site for a truncated protein may occur where indicated by arrow (a), resulting in a protein having a molecular weight of about 23,000 Da. Utilizing the sequence data in FIG. 1, as well as the denoted characteristics of truncated IGFBP-5, it is within the skill of the art to obtain other DNA sequences encoding truncated IGFBP-5. For example, the structural gene may be manipulated by varying individual nucleotides, while retaining the correct amino acid(s), or varying the nucleotides, so as to modify the amino acids, without loss of biological activity. Nucleotides may be substituted, inserted, or deleted by known techniques, including, for example, in vitro mutagenesis and primer repair. The structural gene may be truncated at its 3'-terminus and/or its 5'-terminus while retaining its biological activity.

Exemplified truncations of the present invention include a 23-kDa U-2 human osteosarcoma cell derived IGFBP-5 starting at about amino acid 24 and truncated at about amino acid 163; and a recombinant truncated IGFBP-5 starting at about amino acid 21 and truncated at about amino acid 189 of FIG. 1. By "C-terminus," is meant the carboxyl end region of an IGFBP.

By "decreased affinity," is meant a decrease in the strength of interaction between truncated IGFBPs and IGFS. The affinity is usually characterized by an equilibrium constant, association constant, or dissociation constant for the binding, wherein the binding is the concentration at which half the receptors are occupied. Preferably, the decrease in affinity, measured as the inverse of such a constant, is at least about 50%, and more preferably at least about 75% or 90%.

By "specific binding," it is intended polypeptides that bind with truncated IGFBPs and their derivatives and which have a measurably higher binding affinity for the target polypeptide, i.e., truncated IGFBPs and polypeptide derivatives of truncated IGFBPs, than for unrelated polypeptides tested for binding. Higher affinity by a factor of 10 is preferred, more preferably a factor of 100. Binding affinity for antibodies refers to a single binding event (i.e., monovalent binding of an antibody molecule).

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start-codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki, et al., Nature 324:163 (1986); and Scharf et al., Science (1986) 233:1076–1078; and U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. It is expected that the overall homology between different species or forms of truncated IGFBPS, including truncated IGFBP-5, at the nucleotide level probably will be about 40% or greater, probably about 60% or greater, and even more probably about 80% to about 90% or greater. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

Truncated IGFBPs may be used for producing antibodies, either monoclonal or polyclonal, specific to the truncated IGFBP. The methods for producing these antibodies are known in the art.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "genomic" is meant a collection or library of DNA molecules which are derived from restriction fragments that have been cloned in vectors. This may include all or part of the genetic material of an organism.

By "cDNA" is meant a complimentary mRNA sequence that hybridizes to a complimentary strand of mRNA.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

By "pharmaceutical acceptable carrier," is meant any pharmaceutical carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art. Preferably Calcitonin, a polypeptide hormone produced by C-cells.

The therapeutic compositions typically will contain pharmaceutically acceptable vehicles, such as water, saline, glycerol, ethanol, etc. Additionally, auxiliary substances, such as wetting or emulsifying agents, pH buffering substances, and the like, may be present in such vehicles.

Typically, the therapeutic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect.

By "effective amount," it is meant that the administration of that amount to an individual, either in a single dose or as part of a series, is effective for treatment, as defined above. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation, the treating doctor's assessment of the medical situation, and other relevant factors. It is expected that the amount will fall in a relatively broad range that can be determined through routine trials.

Additional formulations suitable for modes of administration also include oral formulations, mist or nasal sprays, and suppositories. Dosage treatment may be a single dose schedule or a multiple dose schedule.

By "mitogenic," "mitogenetic," or "mitogenesis," is meant the process of stimulating in vitro or in vivo cell division or growth especially as applied to lymphocytes, osteoblasts or other similar cells.

By "osteogenic, " or "osteogenesis" is meant the stimulation in vitro or in vivo of bone tissue division or growth, particularly osteoblasts, or the addition of bone mass.

By "bone disorder," is meant diseases associated with loss of bony tissue such as osteoporosis.

2. Specific Modes for Carrying Out the Invention
a. Sources of Truncated IGFBPs Truncated IGFBPs are derivable from mammals, e.g. murine, porcine, equine, bovine, and human sources. All such sources are included within the definition of truncated IGFBPs, as long as they comply with the required degree of homology. Truncated IGFBPs include binding proteins purified from a tissue extract or from a conditioned culture medium as well as those obtained by recombinant means.

b. Purification of Truncated IGFBPs

Truncated IGFBPs can be readily purified from blood and its components, such as serum and plasma and from cells genetically modified to produce truncated IGFBPs or polypeptide derivatives thereof, by affinity chromatography using a monoclonal antibody specific for a particular truncated IGFBP. In addition to the use of antibody affinity chromatography, truncated IGFBPs and polypeptide derivatives thereof can be purified by a variety of other widely known protein purification techniques (either alone or in combination) including immunoprecipitation, gel filtration, ion exchange chromatography, chromatofocusing, isoelectric focusing, selective precipitation, electrophoresis, and the like. Fractions isolated during purification procedures can be analyzed for the presence of truncated IGFBPs or polypeptide derivatives of truncated IGFBPs by immunoassays employing truncated IGFBPs-specific antibodies or truncated IGFBPs-specific bioassays. A detailed example for truncated IGFBP-5 is provided below in Sections 3a–3b.

c. Isolation of Truncated IGFBP Sequences

Isolation of nucleotide sequences encoding a truncated IGFBP involves creation of either a genomic library prepared from cells encoding truncated IGFBPs or preparation of a cDNA library from RNA isolated from cells expressing a truncated IGFBP. It will generally be preferable to create a cDNA library for isolation of truncated IGFBPs coding nucleotide sequences so as to avoid any possible problems arising from attempts to determine intron/exon borders. Genetic libraries can be made in either eukaryotic or prokaryotic host cells. Widely available cloning vectors such as plasmids, cosmids, phage, YACs and the like can be used to generate genetic libraries suitable for the isolation of nucleotide sequences encoding truncated IGFBP or portions thereof.

d. Screening for the Presence of Truncated IGFBP Sequences

Useful methods for screening genetic libraries for the presence of truncated IGFBP nucleotide sequences include the preparation of oligonucleotide probes based on the N-terminus amino acid sequence information from purified truncated IGFBP or purified internal fragments of purified truncated IGFBP. By employing the standard triplet genetic code, oligonucleotide sequences of about 17 base pairs or longer can be prepared by conventional in vitro synthesis techniques so as to correspond to portions of truncated IGFBPs for which the amino acid sequence has been determined by N-terminus analysis. The resultant nucleic acid sequences can be subsequently labeled with radio-nuclides, enzymes, biotin, fluorescers, or the like, and used as probes for screening genetic libraries.

Additional methods of interest for isolating truncated IGFBPs encoding nucleic acid sequences include screening genetic libraries for the expression of truncated IGFBPs or fragments thereof by means of. truncated IGFBP specific antibodies, either polyclonal or monoclonal. A preferred technique involves the use of degenerate primers based on partial amino acid sequences of purified truncated IGFBPs or on sequences from known related molecules and the polymerase chain reaction (PCR) to amplify gene segments between the primers. The gene can then be isolated using a specific hybridization probe based on the amplified gene segment, which is then analyzed for appropriate expression of protein. A detailed description of this technique is set forth in the examples below in Sections 3a–3b.

e. Sequencing Methods

Nucleotide sequences encoding truncated IGFBPs can be obtained from recombinant DNA molecules recovered from truncated IGFBP genetic library isolates. The nucleotide sequence encoding truncated IGFBPs can be obtained by sequencing the non-vector nucleotide sequences of these recombinant molecules. Nucleotide sequence information can be obtained by employing widely used DNA sequencing protocols, such as Maxim and Gilbert sequencing, dideoxy nucleotide sequencing, and the like. Examples of suitable nucleotide sequencing protocols can be found in Berger and Kimmel, Methods in Enzymology Vol. 52, Guide to Molecular Cloning Techniques, (1987) Academic Press. Nucleotide sequence information from several recombinant DNA isolates, including isolates from both cDNA and genomic libraries, may be combined so as to provide the entire amino acid coding sequence of truncated IGFBPs as well as the nucleotide sequences of introns within the truncated IGFBP gene, upstream nucleotide sequences, and downstream nucleotide sequences.

Nucleotide sequences obtained from sequencing truncated IGFBPs specific genetic library isolates are subjected to analysis in order to identify regions of interest in the truncated IGFBP genes. These regions of interest include open reading frames, introns, promoter sequences, termination sequences, and the like. Analysis of nucleotide sequence information is preferably performed by computer. Software suitable for analyzing. nucleotide sequences for regions of interest is commercially available and includes, for example, DNASIS™ (Pharmacia LKB Technology, Piscataway, New Jersey). It is also of interest to use amino acid sequence information obtained from the N-terminus sequencing of purified truncated IGFBPs when analyzing truncated IGFBPs nucleotide sequence information so as to improve the accuracy of the nucleotide sequence analysis.

f. Expression Systems

Truncated IGFBPs and polypeptide derivatives of truncated IGFBPs can be expressed by recombinant techniques when a DNA sequence encoding the relevant molecule is functionally inserted into a vector. By "functionally inserted" is meant in proper reading frame and orientation, as is well understood by those skilled in the art. When producing a genetic construction containing a complete truncated IGFBPs reading frame, a preferred starting material is a cDNA library isolate encoding truncated IGFBPs. Typically, the truncated IGFBP gene will be inserted downstream from a promoter and will be followed by a stop codon, although production as a hybrid protein followed by cleavage may be used, if desired. In general, host-cell-specific sequences improving the production yield of truncated IGFBP and truncated IGFBP polypeptide derivatives will be used and appropriate control sequences will be added to the expression vector, such as enhancer sequences, polyadenylation sequences, and ribosome binding sites. Once the appropriate coding sequence is isolated, it can be expressed in a variety of different expression systems; for example those used with mammalian cells, baculoviruses, bacteria, and yeast. These are discussed in turn below.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, typically located within 100 to 200 bp upstream of the TATA box. An upstream promoter element determines the rate at which transcription is initiated and can act in either orientation [Sambrook et al. (1989) "Expression of Cloned Genes in Mammalian Cells." In Molecular Cloning: A Laboratory Manual, 2nd ed.].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will typically increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) Science 236:1237; Alberts et al. (1989) Molecular Biology of the Cell, 2nd ed.]. Enhancer elements derived from viruses may be particularly useful, because they typically have a broader host range. Examples include the SV40 early gene enhancer [Dijkema et al (1985) EMBO J. 4:761] and the enhancer/promoters derived from the long terminal repeat (LTR) of the Rous Sarcoma Virus [Gorman et al. (1982b) Proc. Natl. Acad. Sci. 79:6777] and from human cytomegalovirus [Boshart et al. (1985) Cell 41:521]. Additionally, some enhancers are regulatable and become active only in the presence of an inducer, such as a hormone or metal ion [Sassone-Corsi and Borelli (1986) Trends Genet. 2:215; Maniatis et al. (1987) Science 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell. The adenovirus tripartite leader is an example of a leader sequence that provides for secretion of a foreign protein in mammalian cells.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) Cell 41:349; Proudfoot and Whitelaw (1988) "Termination and 3' end processing of eukaryotic RNA. In Transcription and splicing (ed. B. D. Hames and D. M. Glover); Proudfoot (1989) Trends Biochem. Sci. 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In Molecular Cloning: A Laboratory Manual.

Some genes may be expressed more efficiently when introns (also called intervening sequences) are present. Several cDNAs, however, have been efficiently expressed from vectors that lack splicing signals (also called splice donor and acceptor sites) [see e.g., Gothing and Sambrook (1981) Nature 293:620]. Introns are intervening noncoding sequences within a coding sequence that contain splice donor and acceptor sites. They are removed by a process called "splicing," following polyadenylation of the primary transcript [Nevins (1983) Annu. Rev. Biochem. 52:441; Green (1986) Annu. Rev. Genet. 20:671; Padgett et al. (1986) Annu. Rev. Biochem. 55:1119; Krainer and Maniatis (1988) "RNA splicing." In Transcription and splicing (ed. B. D. Hames and D. M. Glover)].

Typically, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) Cell 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2 [Kaufman et al. (1989) Mol. Cell. Biol. 9:946 and pHEBO [Shimizu et al. (1986) Mol. Cell. Biol. 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding a truncated IGFBP can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the truncated IGFBP DNA sequence into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, Texas Agricultural Experiment Station Bulletin No. 1555 (1987) (hereinafter "Summers and Smith"), and incorporated by reference.

Prior to inserting the truncated IGFBP DNA sequence into the baculovirus genome, the above described components, comprising a promoter, leader (if desired), coding sequence of interest, and transcription termination sequence, are typically assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable-host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, Virology (1989) 17:31.

The plasmid usually also contains the polyhedrin polyadenylation signal (Miller et al. (1988) Ann. Rev. Microbiol., 42:177) and a procaryotic ampicillin-resistance (amp) gene and origin of replication for selection and propagation in *E. coli.*

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: The Molecular Biology of Baculoviruses (ed. Walter Doerfler); EPO Pub. Nos. 127,839 and 155,476; and the gene encoding the p10 protein Vlak et al., (1988), J. Gen. Virol. 69:765.

DNA encoding suitable signal sequences can be derived from genes for secreted insect or baculovirus proteins, such as the baculovirus polyhedrin gene (Carbonell et al. (1988) Gene, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), Nature 315:592; human gastrin-releasing peptide, Lebacq-Verheyden et al., (1988), Molec. Cell. Biol. 8:3129; human IL-2, Smith et al., (1985) Proc. Nat'l Acad. Sci. USA, 82:8404; mouse IL-3, (Miyajima et al., (1987) Gene 58:273; and human glucocerebrosidase, Martin et al. (1988) DNA, 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment typically encodes a signal peptide comprised of hydrophobic amino acids which direct the translocation of the protein into the endoplasmic reticulum.

After insertion of the truncated IGFBP DNA sequence and/or the gene encoding the expression product precursor, an insect cell host is co-transformed with the heterologous DNA of the transfer vector and the genomic DNA of wild type baculovirus—usually by co-transfection. The promoter and transcription termination sequence of the construct will typically comprise a 2–5 kb section of the baculovirus genome. Methods for introducing heterologous DNA into the desired site in the baculovirus virus are known in the art. (See Summers and Smith supra; Ju et al. (1987); Smith et al., Mol. Cell. Biol. (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), Bioessays 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly retractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti*, *Autographa californica*, *Bombyx mori*, *Drosophila melanogaster*, *Spodoptera frugiperda*, and *Trichoplusia ni* (PCT Pub. No. WO89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g., Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain truncated IGFBP expression, recombinant host cells derived from the transformants are incubated under conditions which allow expression of the recombinant truncated IGFBP encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980)

Nuc. Acids Res. 8:4057; Yelverton et al. (1981) *Nucl. Acids Res.* 9:731; U.S. Pat. No. 4,738,921; EPO Pub. Nos. 036 776 and 121 775]. The g-laotamase (bla) promoter system [Weissmann (1981) "The cloning of interferon and other mistakes." In Interferon 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophase T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S mRNA [Steitz et al. (1979) "Genetic signals and nucleotide sequences in messenger RNA" In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in Escherichia coli" In *Molecular Cloning: A Laboratory Manual.*

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Pub. No. 219 237).

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from lacZ [Jia et al. (1987) *Gene* 60:197]; trpE [Allen et al. (1987) *J. Biotechnol.* 5:93; Makoff et al. (1989) *J. Gen. Microbiol.* 135:11]; and Chey [EPO Pub. No. 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal'sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (ompA) [Oka et al. (1985) *Proc. Natl. Acad. Sci.* 82:7212]. As an additional example, the signal sequence of the alpha-amylase gene from various Bacilus strains can be used to secrete heterologous proteins from *B. subtilis* [Palva et al. (1982) *Proc. Natl. Acad. Sci. USA* 79:5582; EPO Pub. No. 244 042].

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Pub. No. 127 328). Integrating vectors may also be comprised of bacteriophage or transposon sequences.

Typically, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are typically comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EPO Pub. Nos. 036 259 and 063 953; PCT WO 84/04541]; *Escherichia coli* [Shimatake et al. (1981) *Nature* 292:128; Amann et al. (1985) *Gene* 40:183; Studier et al. (1986) *J. Mol. Biol.* 189:113; EPO Pub. Nos. 036 776, 136 829 and 136 907]; *Streptococcus cremoris* [Powell et al. (1988) *Appl. Environ. Microbiol.* 54:655]; *Streptococcus lividans* [Powell et al. (1988) *Appl. Environ. Microbiol.* 54:655]; *Streptomyces lividans* [U.S. Pat. No. 4,745,056].

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al. (1989) *FEMS Microbiol. Lett.* 60:273; Palva et al. (1982) *Proc. Natl. Acad. Sci. USA* 79:5582; EPO Pub. Nos. 036 259 and 063 953; PCT Publication No. WO84/04541, *Bacillus*], [Miller et al. (1988) *Proc. Natl. Acad. Sci.* 85:856; Wang et al. (1990) *J. Bacteriol.* 172:949, *Campylobacter*]; [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*]; [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*]; [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

iv. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Pub. No. 329 203). The yeast PHOS gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. No. 4,876,197 and U.S. Pat. No. 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Pub. No. 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: Plasmids of Medical. *Environmental and Commercial Importance* (eds. K. N. Timmis and A. Puhler); Mercerau-Puigalon et al. (1980) Gene 11:163; Panthier et al. (1980) *Curr. Genet.* 2:109].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Pub. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (see, e.g., PCT Publ. No. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (EPO Pub. No. 012 873; JPO Pub. No. 62,096,086) and the A-factor gene (U.S. Pat. No. 4,588, 684). Alternatively, leaders of non-yeast origin, such as an interferon leader, exist that also provide for secretion in yeast (EPO Pub. No. 060 057).

A preferred class of secretion leaders are those that employ a fragment of the yeast alpha factor gene, which contains both a "pre" signal sequence, and a "pro" region. The types of alpha factor fragments that can be employed include the full-length pre-pro alpha factor leader (about 83 amino acid residues) as well as truncated alpha-factor leaders (typically about 25 to about 50 amino acid residues) (U.S. Pat. No. 4,546,083 and U.S. Pat. No. 4,870,008; EPO Publ. No. 324 274). Additional leaders employing an alpha-factor leader fragment that provides for secretion include hybrid alpha factor leaders made with a presequence of a first yeast, but a pro-region from a second yeast alpha factor. See e.g., PCT Publ. No. WO89/02463.

Typically, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Typically, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 [Botstein et al. (1979) Gene 8:17–24]; pCl/1 [Brake et al. (1984) Proc. Natl. Acad. Sci USA 81:4642–4646]; and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Enter a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228–245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) Proc. Natl. Acad. Sci. USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Typically, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol. Rev. 51:351].

Alternatively, some of the above described components can be put together into transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans [Kurtz, et al. (1986) Mol. Cell. Biol. 6:142]; Candida maltosa [Kunze, et al. 91985) J. Basic Microbiol. 25:141]; Hansenula polymorpha [Gleeson, et al. (1986) J. Gen. Microbiol. 132:3459; Roggenkamp et al. (1986) Mol. Gen. Genet. 202:302]; Kluyveromyces fragilis [Das, et al. (1984) J. Bacteriol. 158:1165]; Kluyveromyces lactis [De Louvencourt et al. (1983) J. Bacteriol. 154:737; Van den Berg et al. (1990) Bio/Technology 8:135]; Pichia quillerimondii [Kunze et al. (1985) J. Basic Microbiol. 25:141]; Pichia pastoris [Cregg, et al. (1985) Mol. Cell. Biol. 5:3376; U.S. Pat. No. 4,837,148 and U.S. Pat. No. 4,929,555]; Saccharomyces cerevisiae [Hinnen et al. (1978) Proc. Natl. Acad. Sci. USA 75:1929; Ito et al. (1983) J. Bacteriol. 153:163]; Schizosaccharomyces pombe [Beach and Nurse (1981) Nature 300:706]; and Yarrowia lipolytica [Davidow, et al. (1985) Curr. Genet. 10:380–471; Gaillardin, et al. (1985) Curr. Genet. 10:49].

Methods of introducing exogenous DNA into yeast hosts are well-known in the art, and typically include either the transformation of spheroplasts or of intact yeast cells treated with alkali cations. Transformation procedures usually vary with the yeast species to be transformed. See e.g., [Kurtz et al. (1986) *Mol. Cell. Biol.* 6:142; Kunze et al. 91985) *J. Basic Microbiol.* 25:141, *Candida*]; [Gleeson et al. 91986) *J. Gen. Microbiol.* 132:3459; Roggenkamp et al. (1986) *Mol. Gen. Genet.* 202:302, *Hansenula*]; [Das et al. (1984) *J. Bacteriol.* 158:1165; De Louvencourt et al. (1983) *J. Bacteriol.* 154:1165; Van den Berg et al. (1990) *Bio/Technology* 8:135, *Kluyveromyces*]; [Cregg et al. (1985) *Mol. Cell. Biol.* 5:3376; Kunze et al. (1985) *J. Basic Microbiol.* 25:141; U.S. Pat. No. 4,837,148 and U.S. Pat. No. 4,929,555, *Pichia*]; [Hinnen et al. (1978) *Proc. Natl. Acad. Sci. USA* 75;1929; Ito et al. (1983) *J. Bacteriol.* 153:163, *Saccharomyces*]; [Beach and Nurse (1981) *Nature* 300:706, *Schizosaccharomyces*]; [Davidow et al. (1985) *Curr. Genet.* 10:39; Gaillardin et al. (1985) *Curr. Genet.* 10:49, *Yarrowia*].

g. Production of Antibodies to IGFBP Truncations

Antibodies specific for truncated IGFBPs are produced by immunizing an appropriate vertebrate host, e.g., rabbit, with purified truncated IGFBP or polypeptide derivatives thereof, by themselves or in conjunction with a conventional adjuvant. Usually, two or more immunizations will be involved, and blood or spleen will be harvested a few days after the last injection. For polyclonal antisera, the immunoglobulins can be precipitated, isolated and purified by a variety of standard techniques, including affinity purification using truncated IGFBPs attached to a solid surface, such as a gel or beads in an affinity column. For monoclonal antibodies, the splenocytes normally will be fused with an immortalized lymphocyte, e.g., a myeloid cell line, under selective conditions for hybridoma formation. The hybridomas can then be cloned under limiting dilution conditions and their supernatants screened for antibodies having the desired specificity. Techniques for producing antibodies are well known in the literature and are exemplified by the publication *Antibodies: A Laboratory Manual* (1988) eds. Harlow and Lane, Cold Spring Harbor Laboratories Press, and U.S. Pat. No. 4,381,292, U.S. Pat. No. 4,451,570, and U.S. Pat. No. 4,618,577.

For both in vivo use of antibodies to truncated IGFBPs and anti-idiotype antibodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. Epstein-Barr virus can be used to immortalize human lymphocytes or a human fusion partner can be used to produce human-human hybridomas. Primary in vitro immunization with peptides can also be used in the generation of human monoclonal antibodies. Antibodies secreted by the immortalized cells are screened to determine the clones that secrete antibodies of the desired specificity.

h. Diagnostic Methods Using Antigens and Antibodies

The compositions comprising antigens or antibodies of the present invention, as well as the genetic material, can be used in diagnostic assays. Methods for detecting the presence of truncated IGFBPs comprise analyzing a biological sample such as a blood sample, cerebrospinal fluid, or tumor or bone tissue.

Typically, methods for detecting analytes such as binding proteins of the invention are based on immunoassays. Such techniques are well known and need not be described here in detail. Examples include both heterogeneous and homogeneous immunoassay techniques. Both techniques are based on the formation of an immunological complex between the binding protein and a corresponding specific antibody. Heterogeneous assays for truncated IGFBPs typically use a specific monoclonal or polyclonal antibody bound to a solid surface. Sandwich assays are increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. No. 3,817,837, U.S. Pat. No. 4,006,360, and U.S. Pat. No. 3,996,345.

The solid surface reagent in the above assay is prepared by known techniques for attaching protein material to solid support material, such as polymeric beads, dip sticks, or filter material. These attachment methods generally include non-specific adsorption of the protein to the support or covalent attachment of the protein, typically through a free amine group, to a chemically reactive group on the solid support, such as an activate carboxyl, hydroxyl, or aldehyde group.

In a second diagnostic configuration, known as a homogeneous assay, antibody binding to an analyte produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

i. Diagnostic Applications Using Genetic Probes

The genetic material of the invention can itself be used in numerous assays as probes for genetic material present in naturally occurring materials. The analyte can be a nucleotide sequence which hybridizes with a probe comprising a sequence of (usually) at least about 16 consecutive nucleotides, usually 30 to 200 nucleotides, up to substantially the full sequence of the sequences shown above (CDNA sequences). The analyte can be RNA or cDNA. The sample is typically as described in the previous section. A positive result is generally characterized as identifying a genetic material comprising a sequence at least about 70% homologous to a sequence of at least 12 consecutive nucleotides of the sequences given herein, usually at least about 80% homologous to at least about 60 consecutive nucleotides within the sequences, and may comprise a sequence substantially homologous to the full-length sequences. In order to detect an analyte, where the analyte hybridizes to a probe, the probe may contain a detectable label. Probes that are particularly useful for detecting binding proteins are based on conserved regions of these proteins, particularly from amino acids 181–191 (PNCD, using single-letter amino acid codes) and amino acids 212–215 (CWCV) of truncated IGFBP-5. These amino acids are highly conserved in all of the related IGFBPs. Only IGFBP-1 has a difference, a N for a D at position 191.

One method for amplification of target nucleic acids, for later analysis by hybridization assays, is known as the polymerase chain reaction (PCR). The PCR technique can be applied to detecting truncated IGFBPs in suspected samples using oligonucleotide primers spaced apart from each other and based on the genetic sequence set forth herein. The primers are complementary to opposite strands of a double stranded DNA molecule and are typically separated by from about 50 to 450 nucleotides or more (usually not more than 2000 nucleotides). This method entails preparing the specific oligonucleotide primers and then repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula (2n) where n is the number of cycles. Given that the average efficiency per cycle ranges from about 65% to 85%, 25 cycles produce from 0.3 to 4.8 million copies of the target sequence.

One method of choice to determine a truncated IGFBP based on selective amplification employs a pair of single-strand primers derived from non-homologous regions of opposite strands of a DNA duplex fragment. If truncated IGFBP-5 is used, these can be selected from the sequences set forth in FIG. 1. These "primer fragments," which form one aspect of the invention, are prepared from truncated IGFBP fragments such as described above. The method follows the process for amplifying selected nucleic acid sequences as disclosed in U.S. Pat. No. 4,683,202.

j. Assay for Biological Properties of Truncated IGFBPs

The property of binding to an IGF is one of the biological activities of the truncated IGFBPs of the invention. These proteins may be conveniently tested in a binding assay using IGF-I [Rinderknecht, E. and Humbel, R. E., J. Biol. Chem. (1978) 253 2769] or IGF-II [Rinderknecht, E. and Humbel, R. E., FEBS (1978) 89: 283], preferably IGF-II, in a labelled, e.g., iodinated form. For example, such an assay may conveniently include performing a gel electrophoresis (SDS-PAGE) of the proteins of the invention, followed by a Western Blot of the gel, then incubating the blot in the presence of [$^{125}$I] IGF-I or II, washing the blot to remove free IGF-I or -II, and detecting the radioactivity on the blot.

k. Administration, Treatment, and Dosage of Truncated IGFBPs

Therapeutic applications of the truncated IGFBPs of the invention include their use as a single therapeutic agent and their use in combination with an IGF.

Cell proliferation can be assessed by [$^3$H] thymidine incorporation into DNA as described in Andress, D. L., and Birnbaum, R. S. (1991) Biochem. Biophys. Res. Commun. 176, 213–218. Preferably, confluent primary cultures of neonatal (3 day) mouse osteoblast-like cells are dispersed into 96-well plates in DMEM containing 10% FBS and allowed to adhere overnight. The medium is then replaced with serum-free medium for 24 hours, discarded and fresh serum-free medium containing 0.1% BSA and test substances is applied for the final 22 hours of the -assay. Four hours before assay terminatation, 0.5 $\mu$Ci of [methyl-$^3$H] thymidine is added to each well. Cells are then collected with a cell harvester (Skatron, Sterling, Va.) and thymidine incorporation is determined by liquid scintillation counting.

Further, the mitogenic activity of an IGF combined with a binding protein of the invention may be tested as follows: The incorporation of [$^3$H] methylthymidine into CCL 39 cells (Chinese hamster lung fibroblasts) in culture is measured as described by Plouet et al. Cell. Miol. (1984) 30:105. In this assay, cell line CCl 39 is seeded in a plate at 40 000 cells per well in 0.5 ml MEM culture medium (Gibco) containing 10% fetal calf serum 0.1% penicillin, 0.4% streptomcyin and 0.5% fungizone. After 72 hours, incubation at 37° C. in an atmosphere loaded with 5% $CO_2$. Cells are washed with MEM medium in the absence of fetal call serum and then cultured in this medium for 20 hours. At this stage, the cell culture is confluent and an IGF or a binding protein or both together are inoculated, each at a dose of 10 ng to 200 ng culture medium. When added together, the molar ratio must be 1:1. The test sample is incubated at 37° C. for 24 hours and then added with 1 mCi [$^3$H] methylthymidine in 10 ml PBS. After 4 hours incubation, the incorporation of methylthymidine is stopped by washing cells with PBS. Cells are fixed with 0.5 ml trichloroacetic acid (5%) for 30 min., washed with water and finally the cells were lysed with 0.5 ml of NaOH 0.1M for 2 hours at 37° C. Next, 0.5 ml of lysate is transferred into a scintillation flask and mixed with 3 ml of scintillation liquid for measuring b-radioactivity. Truncated IGFBPs potentiate the mitogenic activity of bone cells in the absence or presence of IGFs.

A truncated binding protein of the invention, alone or in combination with an IGF, may be administered by any conventional route suitable, e.g., in the form of tablets or capsules or, e.g., subcutaneously or intravenously in the form of injections or infusions. Furthermore, it may be also used topically, e.g., in the form of ointments or suspensions. Preferably, it can be used as a nasal spray or mist, either alone or in conjunction with a suitable pharmaceutical carrier, e.g., calcitonin.

For all the above indications, the appropriate dosage will of course vary depending upon, for example, the nature and severity of the disorder to be treated and the mode of administration. For example, satisfactory results may be obtained in the treatment of osteoporosis at daily dosages from about to 0.1 mg/kg to 40 mg/kg body weight, preferably from about 0.5 mg/kg to about 20 mg/kg body weight of a truncated IGFBP of the invention. In larger mammals, for example humans, the indicated daily dosage can be from about 5 mg, conveniently administered parenterally, for example once a day. When used in combination with an IGF, the molar ratio of the binding protein to IGF is preferably from 0.1:1 to 5:1, more preferably from 0.5:1 to 2:1, most preferably 1:1.

Pharmaceutical compositions of the invention may be manufactured in any conventional manner [*Remington's Pharmaceutical Sciences* (Mack Pub. Co.)]. These compounds and compositions may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like. Calcitonin or derivatives thereof may also be utilized as an acceptable pharmaceutical carrier. Additionally, an in-frame fusion between a calcitonin gene and a truncated IGFBP may also be prepared.

Although the invention has been described with reference to particular embodiments, methods, construction, and use, it will be apparent to those skilled in the art that various changes and modifications can be made without departing from the invention. Additionally, Applicants have exemplified particular embodiments, methods, constructions, and uses of truncated IGFBP-5 but it should be recognized that other truncated IGFBPs are included within the scope of the present invention.

3. Examples a. Materials and Methods i. Source and Purification of IGFBP-5

U-2 human osteosarcoma cells were obtained from American Type Culture Collection (ATCC), 10801 University Boulevard, Manassas Va. U-2 human osteosarcoma cells were cultured in McCoy's 5a medium supplemented with 5% FBS in a humidified-air atmosphere containing 5% $CO_2$. Once the cultures reached confluence, the medium was replaced with serum-free medium for 24 hours. This medium was discarded and fresh serum-free medium was added to the cultures for 72 hours. This medium was collected, centrifuged to remove cellular debris, and frozen at −20° C. The initial purification steps were performed as described in Andress, D. L., and Birnbaum, R. S. (1991) Biochem. Biophys. Res. Commun. 176, 213–218. Briefly, conditioned medium was acidified and ultrafiltered to remove endogenous IGFs and the retentate was applied to an IGF-I affinity column. The IGFBPs proteins were eluted with 40 ml 0.5M acetic acid, concentrated by Speed Vac and applied to a $C_8$ reversed-phase HPLC column. IGFBP-5 was separated from other proteins with a 15–60% acetonitrile gradient in 0.1% trifluoroacetic acid. Fractions were collected in siliconized glass tubes and dried by Speed Vac. IGF-binding activity was determined by an IGF-I binding assay described previously [Andress, D. L., and Birnbaum, R. S. (1991) Biochem. Biophys. Res. Commun. 176, 213–218, Busby, W. H., Klapper, D. G., and Clemmons, D. R. (1988) J. Biol. Chem. 263, 14203–142101 and protein was estimated using a fluorescamine assay with bovine serum albumin (BSA) standards [Bohlen, P., Stein, S., Dairman, W., and Udenfriend, S. (1973) Arch. Biochem. Biophys. 155, 213–220]. IGFBP-5 purity was confirmed by silver stain of a 10% SDS-polyacrylamide gel and by N-terminal amino acid sequencing of 155 pMol of binding protein. Purified truncated IGFBP-5 was stored in 0.1 M acetic acid at −70° C.

ii. Truncated IGFBP Competitive Binding Studies

IGF binding to truncated IGFBP-5 was analyzed by competitive binding with varying concentrations of unlabeled IGFs. Binding of [$^{125}$I] IGF-I and [$^{125}$I] IGF-II to truncated IGFBP-5 was determined by the same assay method used to monitor binding activity of column fractions [Busby, W. H., Klapper, D. G., and Clemmons, D. R. (1988) J. Biol. Chem. 263, 14203–14210]. Briefly, 20,000 CPM of radiolabeled IGF ([$^{125}$I] IGF-I and [$^{125}$I] IGF-II specific activity, 2000 Ci/mmol) was incubated with 230 ng/ml of the truncated IGFBP-5 and increasing concentration of unlabeled IGF-I and IGF-II in 250 μl of assay buffer (0.1 M HEPES, 0.44 sodium bicarbonate, 0.02% Triton, 0.1% BSA, pH 6.0) overnight at 4° C. Bound and free IGF-tracer were separated by adding 250 μl of 1% human gamma globulin and 500 μl of 25% polyethylene glycol and centrifuging the mixture at 2,000×g for 20 minutes. The pellet was washed with 1 ml of 6.25% polyethylene glycol and the final pellet counted in a gamma counter. Nonspecific binding for [$^{125}$I] IGF-I was <15% and for [$^{125}$I] IGF-II, <20% of the total amount of radiolabel added to the tube.

iii. Mitogenic Assay

Cell proliferation was assessed by [$^3$H] thymidine incorporation into DNA as previously described [Andress, D. L., and Birnbaum, R. S. (1991) Biochem. Biophys. Res. Commun. 176, 213–218]. Briefly, confluent primary cultures of neonatal (3 day) mouse osteoblast-like cells were dispersed into 96-well plates in DMEM containing 10% FBS and allowed to adhere overnight. The medium was then replaced with serum-free medium for 24 hours, discarded, and fresh serum-free medium containing 0.1% BSA and test substances was applied for the final 22 hours of the assay. Four hours before the assay was terminated, 0.5 μCi of [methyl-$^3$H] thymidine was added to each well. Cells were then collected with a cell harvester (Skatron, Sterling, Va.) and thymidine incorporation was determined by liquid scintillation counting. All experiments described below were performed at least twice with similar results.

iv. Cell Binding of Truncated IGFBP-5

Binding of U-2-derived truncated IGFBP-5 to normal osteoblast-like cells was determined using radioiodinated binding protein. IGFBP was iodinated using a previously described procedure [Baxter, R. C., and Martin, J. L. (1986) J. Clin. Invest. 78, 1504–1512]. Briefly, 0.5 mCi [$^{125}$I] NaI was added to 50 μl 0.5M sodium phosphate, pH 7.4, containing 2 μg purified IGFBP-5 and 5 μg chloramine-T for 20 seconds. Sodium metabisulfite (5 μg/μl) was then added and free iodide was separated from radiolabeled protein by ultrafiltration (Ultrafree-MC filter unit, Millipore) [Lipford, G. B., Feng, Q., and Wright, Jr., G. L. (1990) Anal. Biochem. 187, 133–135]. The iodinated IGFBP-5 (estimated specific activity, 90 μCi/μg) was stored under nitrogen at −70° C.

Cell binding studies were performed according to the method of Busby et al. [Busby, W. H., Klapper, D. G., and Clemmons, D. R. (1988) J. Biol. Chem. 263, 14203–14210]. Briefly, confluent monolayers of first passage neonatal mouse osteoblasts in 24-well plates were incubated in serum-free medium for 24 hours. The cells were washed twice with phosphate-buffered saline and then incubated in 250 μl assay buffer (20 mM HEPES, 0.1 mg/ml BSA, pH 7.0) for 2 hours at 4 C with 80,000 CPM [$^{125}$I] IGFBP-5 in the absence or presence of 1200 ng/ml unlabeled IGFBP-5. At the end of the incubation period, the buffer was removed and the cells were rinsed with PBS and solubilized. Cell-surface associated [$^{125}$I] IGFBP was determined by counting the cell lysates in a gamma-counter. In some of the cultures cells were solubilized with electrophoresis sample buffer and the proteins were electrophoresed through a 10% SDS-polyacrylamide gel under non-reducing conditions. [$^{125}$I] IGFBP was identified by autoradiography of the dried gels.

b. Results i. Purification of Truncated IGFBP-5

HPLC purification of the IGF-affinity purified binding proteins resulted in one major and several minor peaks of IGF-binding activity. The major peak of binding activity was isolated in fractions 32–35 where a total of 55 fractions were collected. Fractions 32–35 contained a single 23 kDa protein as was demonstrated by silver stain on SDS-PAGE. Its identity as truncated IGFBP-5 was confirmed by N-terminal amino acid sequencing of binding protein pooled from fractions 32–34. Purity was also confirmed by N-terminal amino acid sequencing of 155 pMol of protein. The overall yield was approximately 20 μg of the binding protein from 2 liters of conditioned medium. The size of the U-2 derived binding protein is smaller than the 28.5 kDa molecular weight, based on the deduced amino acid sequence for IGFBP-5 (Shimasaki, S., Shimonaka, M., Zhang, H. P. and Ling, N. (1991) J. Biol. Chem. 266, 10646–10653]. To ensure that IGF-I from the affinity column did not contaminate the purified preparation, we tested comparable amounts of the affinity column eluate for the presence of IGF-I using a specific radioimmunoassay (performed at Nichols Institute, San Juan Capistrano, Calif.) and found undetectable levels. Similarly, no immunoreactive IGF-I was detected in the purified preparation after removal of the binding protein (920 ng applied) using a $C_{18}$ silica cartridge (Seppak). The limit of detection for this assay is 50 picograms of IGF-I. Finally, we failed to detect amino acid sequences for IGF-I or IGF-II when 155 pMol of truncated IGFBP-5 was sequenced; less than 1 pMol of IGF-I would have been detected by this method.

ii. U-2-derived Truncated IGFBP-5

Competitive IGP-binding curves for U-2 derived IGFBP-5 indicated the U-2 derived IGFBP-5 had similar binding affinities for IGF-I and IGF-II. A concentration of 230 ng/ml (10 nM) of binding protein was used, which gave 31–40% specific binding for [$^{125}$I] IGF-I. Half-maximal displacement of [$^{125}$I] IGF-I occurred with approximately 18 nM IGF-I and half-maximal displacement for [$^{125}$I] IGF-II required 13 nM IGF-II. These values are higher than for other IGF-binding proteins [Martin, J. L., Willetts, K. E., and Baxter, R. C. (1990) J. Biol. Chem. 265, 4124–4130], including our results with human recombinant IGFBP-3 where half-maximal displacement of IGF-I tracer required 1.2 nM IGF-I. This suggests that this truncated form of IGFBP-5 has a relatively lower affinity for the IGFs, consistent with an absent or altered carboxyl-terminus.

To evaluate the role of truncated IGFBP-5 on osteoblast mitogenesis, mouse calvarial cells were exposed to purified binding protein and graded concentrations of IGF-I and IGF-II. As the concentration of IGF was increased, the binding protein enhanced thymidine incorporation. For example, at a concentration of 75 ng/ml, IGF-I thymidine incorporation was increased approximately 4000 cpm by the presence of 230 ng/ml truncated IGFBP-5 compared to about 2000 cpm at 0.75 ng/ml IGF-I. For 100 ng/ml IGF-II, IGFBP-5 increased osteoblast mitogenesis approximately 1200 cpm, a 4-fold increase over that seen with 1 ng/ml.

The stimulation of osteoblast mitogenesis at the low IGF concentrations could possibly have resulted from truncated IGFBP-5 induced thymidine incorporation. To rule out this possibility, truncated IGFBP-5 was tested alone using several concentrations. In further experiments, stimulation of osteoblast mitogenesis by truncated IGFBP-5 where the cultures were maintained in serum-free medium containing 0.1% BSA and incubated overnight with varying concentrations of IGFBP-5, were performed over a several month period with different batches of purified binding protein. Thymidine incorporation was significantly increased 24% and 82% over control at 230 ng/ml and 2300 ng/ml IGFBP-5, respectively. Thus, U-2- derived truncated IGFBP-5 is capable of stimulating mitogenesis without the addition of IGF-I or IGF-II to the culture medium.

iii. Potentiating Effects of Truncated IGFBP-5

Additional experiments were run using truncated IGFBP-5 in the presence or absence of IGF-I and/or IGF-II to demonstrate the potentiating effect on osteoblast mitogenesis. Results showed the mitogenic response to the highest concentration of truncated IGFBP-5 tested, 2300 ng/ml, in the presence or absence of maximum stimulatory concentrations of IGF-I or -II (100 ng/ml each). In this experiment, stimulation of mitogenesis by IGF-I or -II alone was relatively small, 50–75% over control values consistent with bioassay variability. Incubation with the IGFs together resulted in an approximate doubling of thymidine incorporation. The response to truncated IGFBP-5 alone was greater than observed with either IGF alone or IGF together with truncated IGFBP-5 and cell proliferation stimulated by either IGF-I or IGF-II was potentiated by the truncated IGFBP-5. For example, thymidine incorporation was 2–2.5-fold greater than the additive responses of IGF and truncated IGFBP-5 alone and when the two IGFs and truncated IGFBP-5 were co-incubated, thymidine incorporation was over 10-fold greater than with the IGFs alone.

To demonstrate that the response to IGFBP-5 was specific, we examined the effect of full length IGFBP-3 on IGF-I stimulated osteoblast mitogenesis. In contrast to IGFBP-5, there was a dose-dependent inhibition of IGF-I stimulated mitogenesis when purified porcine IGFBP-3 was co-incubated with the cells under conditions of a serum-free medium containing 0.1% BSA incubated overnight with or without 50 ng/ml IGF-I in the presence of varying concentrations of porcine IGFBP-3. Similar results were obtained with recombinant human IGFBP-3 except that complete inhibition of the IGF-I effect was observed at 600 ng/ml as well as at 2000 ng/ml IGFBP-3. These inhibitory results are in agreement with other studies [Knauer, D. J., and Smith, G. L. (1980) Proc. Natl. Acad. Sci.(U.S.A.). 77, 7252–7254], and are believed to be a consequence of IGFBP-3 sequestering IGF in the culture medium.

To rule out the possibility that endogenous IGF production could result in the observed binding protein-stimulated mitogenesis, the following experiment was performed. Radioimmunoassay of IGF-I and IGF-II in media conditioned by the mouse osteoblasts revealed values below the detection limit of the assays (performed by Dr. Ronald Bowsher, Lilly Research Laboratories). In these assays, serum-free medium containing 0.1% BSA conditioned by the mouse cells for 22 hours was extracted by formic acid/Tween-20/acetone to remove binding proteins. IGF-II was measured by immunoassay using a monoclonal antibody and rat IGF-II standard [Bowsher, R. R., Lee, W. H., Apathy, J. M., Smith, M. C., and Henry, D. P. (1991) *Endocrinology* 128, 815–822] and the IGF-I assay utilized a polyclonal rabbit antibody using human IGF-I standards (R. Bow sher, personal communication). The limits of sensitivity for these assays are 5 pg/tube for IGF-II and 3.5 pg/tube for IGF-I. The maximum concentration of IGF-I and IGF-II in the conditioned medium, therefore, did not exceed 3.5 ng/ml and 5 ng/ml, respectively.

Because these amounts of IGF could be sufficient to permit an apparent truncated IGFBP-5 enhancement of thymidine incorporation, we tested the effect of truncated IGFBP-5 in the presence of 2000 ng/ml full length IGFBP-3, a concentration which will inhibit the mitogenic effects of at least 50 ng/ml IGF-I. In addition, because we have found that full length IGFBP-3 has a higher affinity for the IGFs than does the U-2 derived IGFBP-5, sequestration of IGF-I and IGF-II by IGFBP-3 in the assay medium would be the expected response during a co-incubation experiment. In another experiment, IGFBP-3 alone had no effect on basal cell mitogenesis and its presence failed to blunt the stimulatory effect of IGFBP-5. Thus, neither IGF-I nor IGF-II were involved in the stimulatory effect of IGFBP-5.

Because of the possibility that the mitogenic enhancing effects of truncated IGFBP-5 might be related to its ability to associate with the cell, similar to full length IGFBP-1 [Busby, W. H., Klapper, D. G., and Clemmons, D. R. (1988) J. Biol. Chem. 263, 14203–14210], we performed cell-binding experiments with [$^{125}$I] IGFBP-5. Osteoblast cultures treated with [$^{125}$I] IGFBP-5 specifically bound the binding protein as demonstrated by the effective competition with unlabeled IGFBP-5. Specific cell binding of [$^{125}$I] IGFBP-5 was approximately 2% of the total counts added. When the crosslinking agent, disuccinimidyl suberate, was added to the cultures and the cellular proteins were separated by SDS-PAGE, there was a single band of 23–24 kDa and no bands consistent with binding to the IGF receptors (>130 kDa). In addition, there was no band shift from binding of IGF to the binding protein.

4. Deposit of Biological Material

Plasmid pBs24UbBP5-2.2 was deposited by Chiron Corporation, an assignee of the present invention, on Nov. 3, 1992, with the American Type Culture Collection (ATCC), 12301 Parklawn Drive, Rockville, Md., under the terms of the Budapest Treaty on the International Recognition of the Deposit of Microorganisms for purposes of patent procedure. The accession number is 75341.

This deposit is provided as a convenience to those of skill in the art and is not an admission that a deposit is required under 35 U.S.C. 112. The nucleic acid sequence of this plasmid, as well as the amino acid sequence of the polypeptide encoded thereby, are incorporated herein by reference and should be referred to in the event of an error in the sequence described herein. A license may be required to make, use, or sell the deposited material, and no such license is granted hereby.

What is claimed is:

1. A method for stimulating osteogenesis comprising contacting bone tissue with an amount of a composition effective for stimulating osteogenesis of bone cells, said composition comprising a substantially pure truncated insulin-like growth factor binding protein-5 (IGFBP-5), and a pharmaceutically acceptable carrier, wherein the truncated IGFBP-5 is selected from the group consisting of (a) a truncated IGFBP-5 that has the sequence of amino acids depicted at positions 21 through 189, inclusive, of FIGS. 1A–1C (SEQ ID NO:3); and (b) a truncated IGFBP-5 that has the sequence of amino acids depicted at positions 21 through 163, inclusive, of FIGS. 1A–1C (SEQ ID NO:3).

2. A method according to claim 1 wherein the truncated IGFBP-5 has the sequence of amino acids depicted at positions 21 through 163, inclusive, of FIGS. 1A–1C (SEQ ID NO:3).

3. A method according to claim 1 wherein the truncated IGFBP-5 has the sequence of amino acids depicted at positions 21 through 189, inclusive, of FIGS. 1A–1C (SEQ ID NO:3).

4. A method according to claim 1 wherein the truncated IGFBP-5 is capable of stimulating osteogenesis in the absence of an IGF.

5. A method according to claim 1 wherein the substantially pure truncated IGFBP-5 is devoid of other human proteins.

6. A method according to claim 1 wherein the substantially pure truncated IGFBP-5 is recombinantly produced truncated human IGFBP-5.

7. A method according to claim 1 wherein the truncated IGFBP-5 is obtainable from the cell group consisting of a U-2 human osteosarcoma cell, a human glioblastoma tumor cell, and a human fetal dermal fibroblast cell.

8. A method according to claim 1 wherein the truncated IGFBP-5 is obtainable from a U-2 human osteosarcoma cell.

9. A method according to claim 1 wherein the composition further comprises at least one substantially pure IGF.

10. A method according to claim 1 wherein the composition further comprises calcitonin.

11. A method according to claim 1 comprising subcutaneous administering of the composition.

12. A method for stimulating osteogenesis comprising contacting bone tissue with an amount of a composition effective for stimulating osteogenesis of bone cells, said composition comprising a substantially pure truncated insulin-like growth factor binding protein-5 (IGFBP-5), and a pharmaceutically acceptable carrier, wherein the truncated IGFBP-5 has the sequence of amino acids depicted at positions 24 through 163, inclusive, of FIGS. 1A–1C (SEQ ID NO:3).

13. A method for stimulating osteogenesis comprising contacting bone tissue with an amount of a composition effective for stimulating osteogenesis of bone cells, wherein the composition comprises substantially pure truncated human IGFBP-5 derived from U-2 human osteosarcoma cells and having the amino acid sequence of from amino acid 24 to amino acid 163 of FIGS. 1A–1C (SEQ ID NO:3), and a pharmaceutically acceptable carrier.

14. A method for stimulating osteogenesis comprising contacting bone tissue with an amount of a composition effective for stimulating osteogenesis of bone cells, said composition comprising a substantially pure truncated insulin-like growth factor binding protein-5 (IGFBP-5), and a pharmaceutically acceptable carrier, wherein the truncated IGFBP-5 has the sequence of amino acids depicted at positions 1–189, inclusive, of FIGS. 1A–1C (SEQ ID NO:3).

15. A method for stimulating osteogenesis comprising contacting bone tissue with an amount of a composition effective for stimulating osteogenesis of bone cells, said composition comprising a substantially pure truncated insulin-like growth factor binding protein-5 (IGFBP-5), and a pharmaceutically acceptable carrier, wherein the truncated IGFBP-5 has the sequence of amino acids depicted at positions 1–163, inclusive, of FIGS. 1A–1C (SEQ ID NO:3).

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 1650 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GAATTCGGAG ATCTACAGGC TCTCCTGCCC CACCCCGAGG TAAAGGGGGC GACTAAGAGA      60

AGATGGTGTT GCTCACCGCG GTCCTCCTGC TGCTGGCCGC CTATGCGGGG CCGGCCCAGA     120

GCCTGGGCTC CTTCGTGCAC TGCGAGCCCT GCGACGAGAA AGCCCTCTCC ATGTGCCCCC     180

CCAGCCCCCT GGGCTGCGAG CTGGTCAAGG AGCCGGGCTG CGGCTGCTGC ATGACCTGCG     240

CCCTGGCCGA GGGGCAGTCG TGCGGCGTCT ACACCGAGCG CTGCGCCCAG GGGCTGCGCT     300

GCCTCCCCCG GCAGGACGAG GAGAAGCCGC TGCACGCCCT GCTGCACGGC CGCGGGGTTT     360

GCCTCAACGA AAAGAGCTAC CGCGAGCAAG TCAAGATCGA GAGAGACTCC CGTGAGCACG     420

AGGAGCCCAC CACCTCTGAG ATGGCCGAGG AGACCTACTC CCCCAAGATC TTCCGGCCCA     480

AACACACCCG CATCTCCGAG CTGAAGGCTG AAGCAGTGAA GAAGGACCGC AGAAAGAAGC     540

TGACCCAGTC CAAGTTTGTC GGGGGAGCCG AGAACACTGC CCACCCCCGG ATCATCTCTG     600

CACCTGAGAT GAGACAGGAG TCTGAGCAGG GCCCCTGCCG CAGACACATG GAGGCTTCCC     660

TGCAGGAGCT CAAAGCCAGC CCACGCATGG TGCCCCGTGC TGTGTACCTG CCCAATTGTG     720

ACCGCAAAGG ATTCTACAAG AGAAAGCAGT GCAAACCTTC CCGTGGCCGC AAGCGTGGCA     780

TCTGCTGGTG CGTGGACAAG TACGGGATGA AGCTGCCAGG CATGGAGTAC GTTGACGGGG     840

ACTTTCAGTG CCACACCTTC GACAGCAGCA ACGTTGAGTG ATGCGTCCCC CCCCAACCTT     900

TCCCTCACCC CCTCCCACCC CCAGCCCCGA CTCCAGCCAG CGCCTCCCTC CACCCCAGGA     960

CGCCACTCAT TTCATCTCAT TTAAGGGAAA AATATATATC TATCTATTTG AGGAAACTGA    1020

GGACCTCGGA ATCTCTAGCA AGGGCTCAAC TTCGAAAATG GCAACAACAG AGATGCAAAA    1080

AGCTAAAAAG ACACCCCCCC CCTTTAAATG GTTTTCTTTT TGAGGCAAGT TGGATGAACA    1140

GAGAAGGGAA GAGAGGAAGA ACGAGAGGAA GAGAAGGGAA GGAAGTGTTT GTGTAGAAGA    1200

GAGAGAAAGA CGAATAGAGT TAGGAAAAGG AAGACAAGCA GGTGGGCAGG AAGGACATGC    1260

ACCGAGACCA GGCAGGGGCC CAACTTTCAC GTCCAGCCCT GGCCTGGGGT CGGGAGAGGT    1320

GGGCGCTAGA AGATGCAGCC CAGGATGTGG CAATCAATGA CACTATTGGG GTTTCCCAGG    1380

ATGGATTGGT CAGGGGGAGA AAGGAAAAGG CAAAACACTC CAGGACCTCT CCCGGATCTG    1440

TCTCCTCCTC TAGCCAGCAG TATGGACAGC TGGACCCCTG AACTTCCTCT CCTCTTACCT    1500
```

```
GGGCAGAGTG TTGTCTCTCC CCAAATTTAT AAAAACTAAA ATGCATTCCA TTCCTCTGAA    1560

AGCAAAACAA ATTCATAATT GAGTGATATT AAATAGAGAG GTTTTCGGAA GCAGATCTGT    1620

GAATATGAAA TCCTGTAGAT CTCCGAATTC                                     1650

(2) INFORMATION FOR SEQ ID NO:2:

(i) SEQUENCE CHARACTERISTICS:
        (A) LENGTH: 1648 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

TAAGCCTCTA GATGTCCGAG AGGACGGGGT GGGGCTCCAT TTCCCCCGCT GATTCTCTTC      60

TACCACAACG AGTGGCGCCA GGAGGACGAC GACCGGCGGA TACGCCCCGG CCGGGTCTCG     120

GACCCGAGGA AGCACGTGAC GCTCGGGACG CTGCTCTTTC GGGAGAGGTA CACGGGGGGG    180

TCGGGGACC CGACGCTCGA CCAGTTCCTC GGCCCGACGC CGACGACGTA CTGGACGCGG     240

GACCGGCTCC CCGTCAGCAC GCCGCAGATG TGGCTCGCGA CGCGGGTCCC CGACGCGACG    300

GAGGGGGCCG TCCTGCTCCT CTTCGGCGAC GTGCGGGACG ACGTGCCGGC GCCCCAAACG    360

GAGTTGCTTT CTTCGATGGC GCTCGTTCAG TTCTAGCTCT CTCTGAGGGC ACTCGTGCTC    420

CTCGGGTGGT GGAGACTCTA CCGGCTCCTC TGGATGAGGG GGTTCTAGAA GGCCGGGTTT    480

GTGTGGGCGT AGAGGCTCGA CTTCCGACTT CGTCACTTCT TCCTGGCGTC TTTCTTCGAC    540

TGGGTCAGGT TCAAACAGCC CCCTCGGCTC TTGTGACGGG TGGGGGCCTA GTAGAGACGT    600

GGACTCTACT CTGTCCTCAG ACTCGTCCCG GGGACGGCGT CTGTGTACCT CCGCAGGGAC    660

GTCCTCGAGT TTCGGTCGGG TGCGTACCAC GGGGCACGAC ACATGGACGG GTTAACACTG    720

GCGTTTCCTA AGATGTTCTC TTTCGTCACG TTTGGAAGGG CACCGGCGTT CGCACCGTAG    780

ACGACCACGC ACCTGTTCAT GCCCTACTTC GACGGTCCGT ACCTCATGCA ACTGCCCCTG    840

AAAGTCACGG TGTGGAGGCT GTCGTCGTTG CAACTCACTA CGCAGGGGGG GGTTGGAAAG    900

GGAGTGGGGG AGGGTGGGGG TCGGGCTGA GGTCGGTCGC GGAGGGAGGT GGGGTCCTGC    960

GGTGAGTAAA GTAGAGTAAA TTCCCTTTTT ATATATAGAT AGATAAACTC CTTTGACTCC   1020

TGGAGCCTTA GAGATCGTTC CCGAGTTGAA GCTTTTACCG TTGTTGTCTC TACGTTTTTC   1080

GATTTTTCTG TGGGGGGGGG AAATTTACCA AAAGAAAAAC TCCGTTCAAC CTACTTGTCT   1140

CTTCCCTTCT CTCCTTCTTG CTCTCCTTCT CTTCCCTCTC TTCACAAACA CATCTTCTCT   1200

CTCTTTCTGC TTATCTCAAT CCTTTTCCTT CTGTTCGTCC ACCCGTCCTT CCTGTACGTG   1260

GCTCTGGTCC GTCCCCGGGT TGAAAGTGCA GGTCGGACC GGACCCCAGC CCTCTCCACC   1320

CGCGATCTTC TACGTCGGGT CCTACACCGT TAGTTACTGT GATAACCCCA AAGGGTCCTA   1380

CCTAACCAGT CCCCCTCTTT CCTTTTCCGT TTTGTGAGGT CCTGGAGAGG GCCTAGACAG   1440

AGGAGGAGAT CGGTCGTCAT ACCTGTCGAC CTGGGGACTT GAAGGAGAGG AGAATGGACC   1500

CGTCTCACAA CAGAGAGGGG TTTAAATATT TTTGATTTTA CGTAAGGTAA GGAGACTTTC   1560

GTTTTGTTTA AGTATTAACT CACTATAATT TATCTCTCCA AAAGCCTTCG TCTAGACACT   1620

TATACTTTAG GACATCTAGA GGCTTAAG                                      1648

(2) INFORMATION FOR SEQ ID NO:3:
```

```
    (i) SEQUENCE CHARACTERISTICS:
        (A) LENGTH: 272 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Val Leu Leu Thr Ala Val Leu Leu Leu Ala Ala Tyr Ala Gly
1               5                   10                  15

Pro Ala Gln Ser Leu Gly Ser Phe Val His Cys Glu Pro Cys Asp Glu
            20                  25                  30

Lys Ala Leu Ser Met Cys Pro Pro Ser Pro Leu Gly Cys Glu Leu Val
                35                  40                  45

Lys Glu Pro Gly Cys Gly Cys Cys Met Thr Cys Ala Leu Ala Glu Gly
        50                  55                  60

Gln Ser Cys Gly Val Tyr Thr Glu Arg Cys Ala Gln Gly Leu Arg Cys
65                      70                  75                  80

Leu Pro Arg Gln Asp Glu Glu Lys Pro Leu His Ala Leu Leu His Gly
                85                  90                  95

Arg Gly Val Cys Leu Asn Glu Lys Ser Tyr Arg Glu Gln Val Lys Ile
                100                 105                 110

Glu Arg Asp Ser Arg Glu His Glu Glu Pro Thr Thr Ser Glu Met Ala
        115                 120                 125

Glu Glu Thr Tyr Ser Pro Lys Ile Phe Arg Pro Lys His Thr Arg Ile
        130                 135                 140

Ser Glu Leu Lys Ala Glu Ala Val Lys Lys Asp Arg Arg Lys Lys Leu
145                 150                 155                 160

Thr Gln Ser Lys Phe Val Gly Gly Ala Glu Asn Thr Ala His Pro Arg
                165                 170                 175

Ile Ile Ser Ala Pro Glu Met Arg Gln Glu Ser Glu Gln Gly Pro Cys
                180                 185                 190

Arg Arg His Met Glu Ala Ser Leu Gln Glu Leu Lys Ala Ser Pro Arg
                195                 200                 205

Met Val Pro Arg Ala Val Tyr Leu Pro Asn Cys Asp Arg Lys Gly Phe
                210                 215                 220

Tyr Lys Arg Lys Gln Cys Lys Pro Ser Arg Gly Arg Lys Arg Gly Ile
225                 230                 235                 240

Cys Trp Cys Val Asp Lys Tyr Gly Met Lys Leu Pro Gly Met Glu Tyr
                245                 250                 255

Val Asp Gly Asp Phe Gln Cys His Thr Phe Asp Ser Ser Asn Val Glu
                260                 265                 270
```